United States Patent
Babel

(10) Patent No.: US 6,625,548 B2
(45) Date of Patent: Sep. 23, 2003

(54) MEASURING DEVICE FOR DETERMINING PHYSICAL AND CHEMICAL PROPERTIES OF GASES, LIQUIDS AND SOLIDS

(75) Inventor: Wolfgang Babel, Weil der Stadt (DE)

(73) Assignee: Endress + Hauser Conducta Gesellschaft für Mess- und Regeltechnik mbH + Co., Gerlingen (DE)

(*) Notice: Subject to any disclaimer, the term of this patent is extended or adjusted under 35 U.S.C. 154(b) by 0 days.

(21) Appl. No.: 10/196,137

(22) Filed: Jul. 17, 2002

(65) Prior Publication Data

US 2002/0183939 A1 Dec. 5, 2002

Related U.S. Application Data

(63) Continuation of application No. 09/391,510, filed on Sep. 8, 1999.
(60) Provisional application No. 60/099,344, filed on Sep. 8, 1998.

(51) Int. Cl.[7] .............................................. E21B 49/02
(52) U.S. Cl. ........................ 702/22; 702/31; 702/23; 702/30; 702/182; 702/188; 702/189
(58) Field of Search ........................ 702/22–24, 27–29, 702/30–32, 45, 47, 49, 50, 55, 98–100, 108, 114, 124, 127, 130, 136, 138, 140, 182, 183, 188, 189, FOR 115–121, FOR 134–135, FOR 142–143, FOR 170–171; 73/25.01; 422/62; 700/266, 2, 3

(56) References Cited

U.S. PATENT DOCUMENTS

| | | | | | |
|---|---|---|---|---|---|
| 3,800,090 | A | * | 3/1974 | Matena | 379/33 |
| 4,573,115 | A | * | 2/1986 | Halgrimson | 700/9 |
| 5,495,769 | A | * | 3/1996 | Broden et al. | 700/129 |
| 5,671,273 | A | * | 9/1997 | Lanquist | 379/413.04 |
| 5,909,493 | A | * | 6/1999 | Motoyama | 713/154 |
| 5,923,557 | A | * | 7/1999 | Eidson | 702/121 |
| 6,031,455 | A | * | 2/2000 | Grube et al. | 340/539 |
| 6,073,063 | A | * | 6/2000 | Leong Ong et al. | 73/23.2 |
| 6,104,495 | A | * | 8/2000 | Sieben et al. | 356/432 |
| 6,220,371 | B1 | * | 4/2001 | Sharma et al. | 175/50 |
| 6,244,096 | B1 | * | 6/2001 | Lewis et al. | 73/23.2 |
| 6,252,689 | B1 | * | 6/2001 | Sharp | 359/168 |
| 6,285,964 | B1 | * | 9/2001 | Babel et al. | 702/121 |
| 6,350,369 | B1 | * | 2/2002 | Lewis et al. | 205/777.5 |
| 6,405,030 | B1 | * | 6/2002 | Suprunov | 455/410 |
| 2002/0005580 | A1 | * | 1/2002 | Goodman et al. | 257/734 |
| 2002/0013664 | A1 | * | 1/2002 | Strackeljan et al. | 702/34 |

FOREIGN PATENT DOCUMENTS

EP 190399 A2 * 8/1986 ............ H04Q/9/00

* cited by examiner

Primary Examiner—Marc S. Hoff
Assistant Examiner—Carol S W Tsai
(74) Attorney, Agent, or Firm—Paul Vincent

(57) ABSTRACT

A measuring system for determining physical and chemical properties of gases, liquids and solids includes a computing unit which is coupled with at least one sensor by means of a high capacity communications network. The system eliminates the need for dedicated cabling between the sensor and the computing unit.

19 Claims, 1 Drawing Sheet

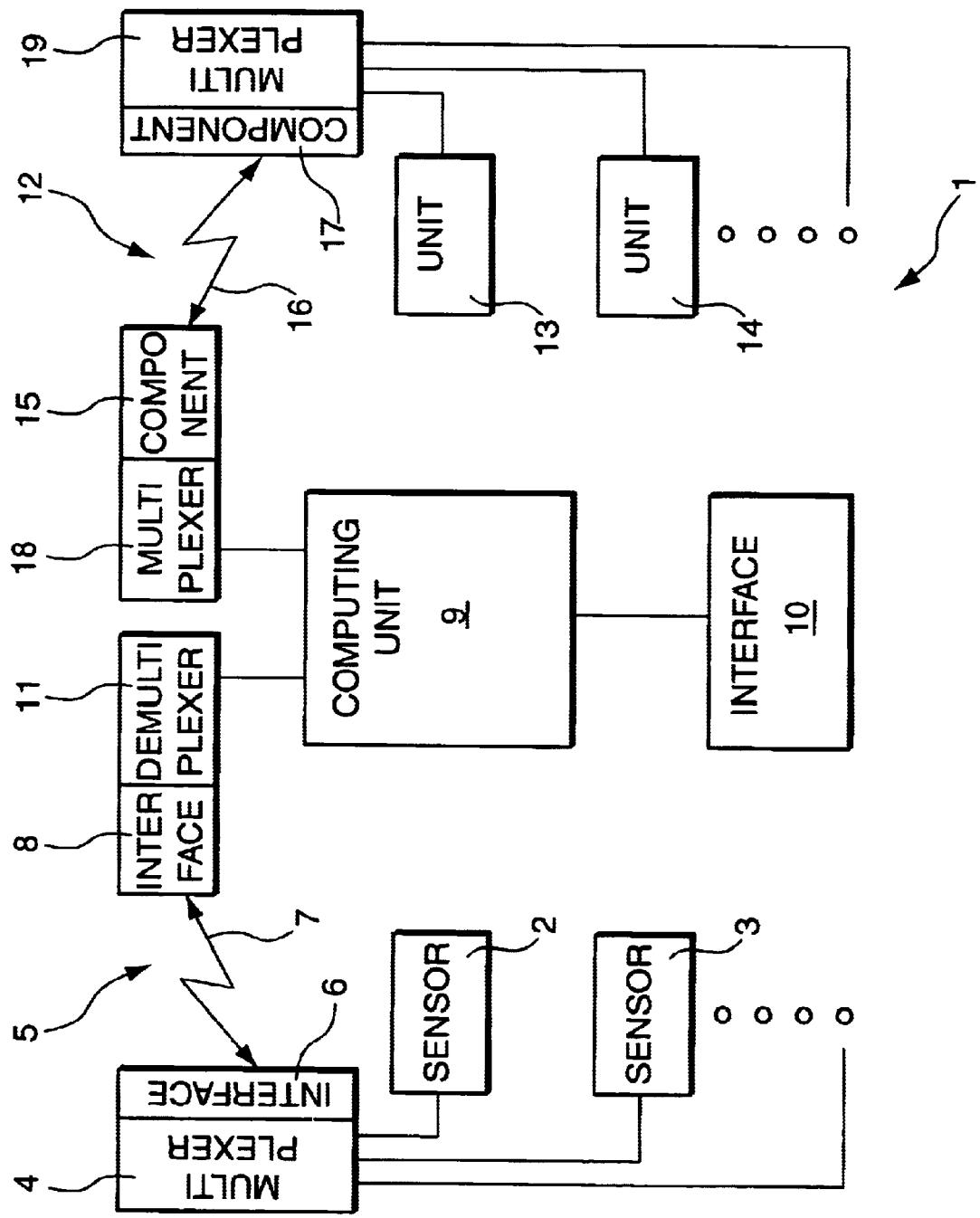

MEASURING DEVICE FOR DETERMINING PHYSICAL AND CHEMICAL PROPERTIES OF GASES, LIQUIDS AND SOLIDS

This application claims benefit of provisional application No. 60/099,344 filed Sep. 8, 1998 as well as a continuation of application Ser. No. 09/391,510 filed on Sep. 8, 1999, the entire disclosure of which are hereby incorporated by reference.

BACKGROUND OF THE INVENTION

The invention relates to a measuring device for determining physical and chemical properties of gases, liquids and solids, having a computing unit which is connected to a sensor. The invention also relates to a method for determining physical and chemical properties of gases, liquids and solids, wherein the measured data are passed on by a sensor to a computing unit.

Such a measuring device and such a method are generally known in the field of measuring technology and are commercially available, in particular for liquid and gas analysis.

The sensor of such a measuring device can be a pH value sensor or a temperature sensor which is e.g. submerged in a liquid to be analyzed. The raw sensor data are processed by an electrical circuit into measured data for subsequent transmission to the computing unit. The measured data can be displayed on an associated monitor with the aid of the computing unit, or can be passed on to another device such as a control station.

In large industrial installations such as treatment plants, a multitude of sensors are connected to a computing unit. The measured data are transmitted through connecting cables especially strung for this purpose. The substantial efforts required in laying the cables result in substantial costs associated with both their installation and maintenance.

In view of the above mentioned prior art, it is the object of the present invention to provide a measuring device and a method for determining physical and chemical properties of gases, liquids and solids, which minimizes installation efforts and associated expenses therefore.

SUMMARY OF THE INVENTION

This object is achieved by the invention with regard to a measuring device of the above-mentioned type, in that the computing unit and the sensor are connected to each other by means of a high capacity communications network. With regard to a method of the above mentioned kind, the object in accordance with the invention is achieved in that the measured data are transmitted via such a high capacity communications network.

In accordance with the invention, the cable connection or connections between the sensor or sensors and the computing unit are replaced by a high capacity communications network. In consequence thereof, a dedicated cable system is no longer needed. The work required for cable system installation and its maintenance is therefore avoided. This represents a considerable advantage for both installation of the measuring device in accordance with the invention as well as for its maintenance with considerable cost savings being achieved.

In advantageous embodiments of the measuring device and the method in accordance with the invention, the computing unit and the sensor are connected to each other for transmission of the measured data via a radio network connection, a telephone network connection, an internet connection, an intranet connection or via a communications connection overlaid on an electrical power grid network.

The connection between the computing unit and the sensor using such a high capacity communications network and the transmission of the measured data via that communications network can therefore be achieved through use of one or more of the above mentioned networks. For such networks, transmission in accordance with the invention has the advantage of avoiding the need to completely construct a specific, dedicated communications link. Instead, a pre-existing communications network can be utilized. For example, for straightforward transmission of the measured data by telephone, a modem or the like can be provided at both ends of a telephone line, to feed and extract the measured data into and out of the telephone network. Such modems are inexpensive and commercially available. Similar considerations apply to transmission of the measured data via either the internet or an intranet system.

A further advantage of use of a communications network media in accordance with the invention is that such a telephone or internet connection permits arbitrary locations to be connected to each other thereby facilitating transmission of the measured data to any desired location. In comparison with the known dedicated cable-connected measuring device, this represents a considerable advantage with regard to the flexibility and applications of the method and device in accordance with the present invention.

In an advantageous further embodiment of the invention, the computing unit is coupled to a further unit, such as a control station activating device. For such embodiments, the computing unit and the further unit can also be connected to each other via a high capacity communications network to allow data and program packages to be exchanged between the computing unit and the further unit via that network link.

These above mentioned data or program packages could include lists of measured data, already processed measured data, measured data to be filed, or the like, and can be passed from the computing station to, for example, a control unit. The data and/or program packages might also be programs which are transmitted from the control station to the computing unit to, for example, update an existing computing unit program. No cable system is needed to transmit such data and/or program packages between the computing unit and the further unit. To this extent the measuring device and method in accordance with the invention are considerably simplified compared to conventional systems.

The computing unit and the further unit can be advantageously connected to each other for transmission of the measured data via a radio connection, a telephone connection, an internet connection, an intranet connection, or a communications connection overlaid on a electrical power grid. In this manner, existing communications media can be utilized in the measuring device in accordance with the invention.

In a further advantageous embodiment of the measuring device and method in accordance with the invention, several sensors and/or several further units are coupled to the computing unit by means of a multiplexer or the like. Commercially available multiplexers and demultiplexers can be used, either in the form of hardware products or as software modules. The measured data, other data, and/or program packages can thereby be transmitted from the sensors to the computing unit and from the computing unit to a further unit with the aid of such multiplexers and demultiplexers.

It is particularly advantageous when the computing unit is a personal computer. Specialized and expensive computing devices are thereby avoided through use of a commercially available personal computer. Program packages, required for example for evaluating the measured data generated by the sensors, can be installed on such a personal computer as can program packages which may be useful for generating lists of the measured data or the like.

The personal computer may be provided with a modem to facilitate transmission of the measured data from the sensors to the personal computer and to facilitate data transmission from the personal computer to further units. The modem can establish a telephone, internet and/or intranet connection.

In this manner, all commercially available options of the personal computer can be utilized for the device and method in accordance with the invention. The measuring device in accordance with the invention can thereby be expanded in a simple and cost-effective manner for accommodating the respective application.

The measuring device and method in accordance with the invention are particularly advantageous in liquid and gas analysis and for measuring moisture in liquids or gases. For such applications, avoidance of the conventional dedicated cable system is particularly advantageous.

Further characteristics, applications and advantages of the invention ensue from the following description of exemplary embodiments of the invention represented in the drawing. All of the elements described and represented constitute inventive subject manner individually or in any arbitrary combination, regardless of their particular combination in the claims and independent of the wording, or embodiments of the descriptions, and the drawings.

BRIEF DESCRIPTION OF THE DRAWINGS

The sole FIGURE is a schematic block diagram of an exemplary embodiment of a measuring device in accordance with the invention.

DESCRIPTION OF THE PREFERRED EMBODIMENT

The FIGURE illustrates a measuring device 1, which is suitable for determining physical and chemical properties of gases, liquids and solids. In particular, the measuring device 1 can be employed for liquid and gas analyses and for measuring moisture in liquids and gases.

The measuring device 1 has one or several sensors 2, 3. These sensors can be pressure sensors, flow-through sensors, filling level sensors, pH value sensors, cloudiness sensors, temperature sensors, sensors for measuring chlorine or chlorine dioxide content, sensors for measuring oxygen content, conductibility sensors, and/or moisture sensors.

The sensors 2,3 are suitable for generating associated measured data. If required, electrical circuits cooperate with the sensors 2, 3, to convert the raw data directly measured by the sensors into measured data. The respective measured data are then available at the outputs of the sensors 2, 3.

The measuring device 1 has a conventional multiplexer 4, to which the sensors 2, 3 are connected. The multiplexer 4 is provided to sequentially poll the data measured by the sensors 2, 3 and to reorganize that data into a common signal.

A communications network 5 is connected downstream of the multiplexer 4, having an interface 6, a transmission path 7 and an interface 8.

By way of example, the communications network 5 can be a radio connection. In this case the interface 6 comprises a transmitter and the interface 8 a receiver. The common signal from the multiplexer 4, containing the measured data of the sensors 2, 3 can then be transmitted via the transmission path 7 by the transmitter 6 to the receiver 8.

The communications medium 5 can also be a telephone or internet connection. In this case, the interfaces 6 and 8 include, for example, a modem. The common signal, composed of the measured data from the sensors 2, 3 and generated by the multiplexer 4, can then be transmitted across the transmission path 7 and between the two modems. Such a communications network 5 permits world-wide transmission of the sensor data.

If the communications medium 5 generates a telephone connection, the measured data can be continuously transmitted via a dedicated telephone line. If the communications medium generates an internet connection, conversion of the measured data into corresponding digital signals is effected and these digital signals are then transmitted via the electronic internet network. Real time operation can be utilized if appropriate.

It is also possible to establish a network connection using the existing electrical power grid as the communications network 5. In this case, the interfaces 6 and 8 convert the signals to be transmitted into high-frequency signals and overlay these signals on the existing electrical power network. In this manner, the measured data can be transmitted within an existing electrical power grid.

The measuring device 1 includes a computing unit 9, preferably, a personal computer. The computing unit 9 has an interface 10, preferably including a monitor and a keyboard. A demultiplexer 11 is also coupled to the computing unit 9 and communicates with the component 8. The signals received by the component 8 are decoded by the demultiplexer 11 and converted into the measured data of the sensors 2, 3. Thus, the measured data of the sensors 2, 3 can be processed by the computing unit 9 in any desired manner.

The multiplexer 4 as well as the demultiplexer 11 can be either hardware components or software modules. The multiplexer 4 and the demultiplexer 11 may also be suitable for performing transmission in the opposite direction, i.e. from the computing unit 9 to the sensors 2, 3.

The component 8 can be designed as a plug-in card of the computing unit 9, preferably of a personal computer. In optional association with a telephone or internet connection, the interface 8 may include a modular, pluggable modem.

The multiplexer 4 and the component 6 can be a process-controlled transmission unit and may also comprise a personal computer having a plugged-in modem.

Should only one single sensor be used, the multiplexer and demultiplexer can be eliminated. In this case the single sensor is directly connected to the computing unit 9 by means of the communications network.

The computing unit 9 can communicate with one or with several further units 13, 14 by means of a further communications network 12. These further units 13, 14 can be control stations, a so-called profi-bus or the like. The further units 13, 14 may also control or regulate a process involving a gas or liquid which is being analyzed with the assistance of sensors 2, 3.

The communications network 12 has a component 15, a transmission path 16 and a component 17. A multiplexer/demultiplexer 18 is connected between the component 15 and the computing unit 9. A multiplexer/demultiplexer 19 is connected between the component 17 and the further units 13, 14.

The communications network 12 can be a telephone network connection, an internet or intranet connection, or a communications connection utilizing an electrical power grid. The components 15 and 17 can be modems and the multiplexers/demultiplexers 18, 19 can be hardware components or software modules.

Data and program packages can be transmitted from the computing unit 9 to the further units 13, 14 and back with the aid of the communications network 12 and the multiplexer/demultiplexer 18, 19 by radio, telephone, internet, intranet or via an electrical power grid. Such data or program packages can include processed measured data (e.g. lists of measured data) or programs which are entered into the computing unit 9 by the further units 13, 14.

Should only one further unit 13, 14 be used the multiplexer/demultiplexer 18, 19 can be eliminated. In this case, the data and/or program packages are directly transmitted from the computing unit 9 to the further unit 13, or vice versa.

If the communications medium 12 is a telephone connection or an internet connection, the modems required therefor can also be plugged into the computing unit 9 (preferably a personal computer) in the form of plug-in cards.

During operation of the described measuring device 1, the measured data generated by the sensors 2, 3 are transmitted via the communications network 5 for processing by the computing unit 9. Data packages generated by the computing unit 9 are then transmitted, via the communications network 12, to the further unit 13 or further units 13, 14. These further units 13, 14 may also be used to update programs in the computing unit 9 via this transmission link.

What is claimed is:

1. A measuring system for determining a chemical or physical property of a gaseous, liquid or solid medium, the system comprising:

a stationary holding means;

at least one sensor mounted to said stationary holding means to contact the medium, said sensor consisting essentially of means for detecting the chemical or physical property of the medium, means for generating at least one electrical signal having at least one signal properly which provides quantitative information concerning the chemical or physical property to be determined and a one-way, output only sensor interface for output of said electrical signal;

an analyzer unit, said analyzer unit accepting input concerning said electrical signal from said sensor, said analyzer unit having means for processing said signal property to extract said quantitative information; and a multiple input and multiple output communications network disposed between and connecting said sensor interface and said analyzer unit to transmit said signal property from said sensor to said analyzer unit, said communications network having switching means for connecting together a selected one of said multiple inputs with selected one of said multiple outputs, said network generating an input-output connection for transmitting that signal property, wherein said communications network has a total number of possible input-output connections defining an overall communication capacity which greatly exceeds a communication capacity required for transmission of said signal property alone.

2. The measuring system of claim 1, wherein said communication network is one of a radio network, a telephone network, an internet network, an intranet network, and a power grid network.

3. The measuring system of claim 1, wherein said analyzer unit comprises a personal computer.

4. The measuring system of claim 1, wherein said sensor is one of a liquid analysis sensor, a gas analysis sensor, a liquid moisture sensor and a gas moisture sensor.

5. The measuring system of claim 1, wherein said sensor is one of a pressure sensor, a flow sensor, a filling level sensor, a pH value sensor, a cloudiness sensor, a temperature sensor, a chlorine content sensor, a chlorine dioxide sensor, an oxygen content sensor, a conductivity sensor, and a moisture sensor.

6. The measuring system of claim 1, wherein a plurality of sensors are provided, each sensor for measuring at least one of a plurality of physical or chemical properties, and further comprising multiplexer means disposed between and connecting said plurality of sensors and said communications network.

7. The measuring system of claim 1, further comprising at least one actuator, said actuator generating a mechanical or electrical output in response to reception of said quantitative information extracted by said analyzer unit, and also further comprising a second multiple input and multiple output communications network disposed between and connecting said actuator and said analyzer unit to transmit said quantitative information from said analyzer unit to said actuator, said second communications network having switching means for connecting together a selected one of said multiple inputs with a selected one of said multiple outputs to create an input-output connection for transmitting said quantitative information, a total plurality of possible input-output connections of said second communications network defining an overall communication capacity for said second communications network, which greatly exceeds a communication capacity required for transmission of said quantitative information alone.

8. The measuring system of claim 7, wherein said second communication network is one of a radio network, a telephone network, an internet network, an intranet network, and a power grid network.

9. The measuring system of claim 7, wherein said analyzer unit comprises a personal computer.

10. The measuring system of claim 7, wherein said sensor is one of a liquid analysis sensor, a gas analysis sensor, a liquid moisture sensor and a gas moisture sensor.

11. The measuring system of claim 7, wherein said sensor is one of a pressure sensor, a flow sensor, a filling level sensor, a pH value sensor, a cloudiness sensor, a temperature sensor, a chlorine content sensor, a chlorine dioxide sensor, an oxygen content sensor, a conductivity sensor, and a moisture sensor.

12. The measuring system of claim 7, wherein a plurality of sensors are provided, each sensor for measuring at least one of a plurality of physical or chemical properties, and further comprising multiplexer means disposed between and connecting said plurality of sensors and said communications network.

13. The measuring system of claim 12, wherein a plurality of actuators are provided, each actuator for generating at least one of a plurality of activities in response to said plurality of physical or chemical properties, and further comprising a second multiplexer means disposed between and connecting said plurality of actuators and said second communications network.

14. A method for determining a chemical or physical property of a gaseous, liquid of solid medium, the method comprising the steps of:

mounting at least one sensor to a stationary holding means to contact a medium, said sensor consisting essentially of means for detecting the chemical or physical property of the medium, means for generating at least one electrical signal having at least one signal property which provides quantitative information concerning the chemical or physical property to be determined, and a one-way output only sensor interface for output of said electrical signal;

configuring an analyzer unit to accept input concerning said electrical signal from said sensor, said analyzer unit having means for processing said signal property to extract said quantitative information; and connecting a multiple input and multiple output communications network between said sensor interface and analyzer unit to transmit said signal property from said sensor to said analyzer unit, said communications network having switching means for connecting together a selected one of said multiple inputs with the selected one of said multiple outputs, said network generating an input-output connection for transmitting said signal property, wherein said communication network has a total number of possible input-output connections defining an overall communications capacity for said communications network which greatly exceeds a communication capacity required for transmission of said signal property alone.

15. The method of claim 14, wherein said communication network is one of a radio network, a telephone network, an internet network, an intranet network, and a power grid network.

16. The method of claim 14, wherein said analyzer unit comprises a personal computer.

17. The method of claim 14, wherein said sensor is one of a liquid analysis sensor, a gas analysis sensor, a liquid moisture sensor and a gas moisture sensor.

18. The method of claim 14, wherein said sensor is one of a pressure sensor, a flow sensor, a filling level sensor, a pH value sensor, a cloudiness sensor, a temperature sensor, a chlorine content sensor, a chlorine dioxide sensor, an oxygen content sensor, a conductivity sensor, and a moisture sensor.

19. The method of claim 14, further comprising configuring at least one actuator to generate a mechanical or electrical output in response to reception of said quantitative information extracted by said analyzer unit, and also further comprising disposing a second multiple input and multiple output communications network to connect said actuator to said analyzer unit for transmitting said quantitative information from said analyzer unit to said actuator, said second communications network having switching means for connecting together a selected one of said multiple inputs with a selected one of said multiple outputs to create an input-output connection for transmitting said quantitative information, a total plurality of possible input-output connections defining an overall communication capacity for said second communications network which greatly exceeds a communication capacity required for transmission of said quantitative information alone.

* * * * *